US012778692B2

(12) United States Patent
Park et al.

(10) Patent No.: US 12,778,692 B2
(45) Date of Patent: Nov. 3, 2026

(54) METHOD FOR SYNCHRONIZING MICROROBOT OPERATION CONTROL AND POSITION RECOGNITION USING DUAL HYBRID ELECTROMAGNET MODULE

(71) Applicant: KOREA INSTITUTE OF MEDICAL MICROROBOTICS, Gwangju (KR)

(72) Inventors: Jong Oh Park, Gyeonggi-do (KR); Ja Young Kim, Daejeon (KR); Manh Cuong Hoang, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 159 days.

(21) Appl. No.: 18/868,961

(22) PCT Filed: Aug. 21, 2023

(86) PCT No.: PCT/KR2023/012319
§ 371 (c)(1),
(2) Date: Nov. 25, 2024

(87) PCT Pub. No.: WO2024/043635
PCT Pub. Date: Feb. 29, 2024

(65) Prior Publication Data

US 2025/0318884 A1 Oct. 16, 2025

(30) Foreign Application Priority Data

Aug. 24, 2022 (KR) ........................ 10-2022-0106039

(51) Int. Cl.
*A61B 34/30* (2016.01)
*A61B 34/00* (2016.01)

(52) U.S. Cl.
CPC .............. *A61B 34/30* (2016.02); *A61B 34/72* (2016.02); *A61B 34/73* (2016.02); *A61B 2034/731* (2016.02)

(58) Field of Classification Search
None
See application file for complete search history.

(56) References Cited

U.S. PATENT DOCUMENTS

2010/0212676 A1 8/2010 Shapiro et al.

FOREIGN PATENT DOCUMENTS

KR 10-2007-0086118 A 8/2007
KR 10-2012-0007296 A 1/2012
(Continued)

OTHER PUBLICATIONS

Liu et al., "Three-Dimensional Localization of a Robotic Capsule Endoscope Using Magnetoquasistatic Field", published Jul. 28, 2020. (Year: 2020).*
(Continued)

*Primary Examiner* — Christopher A Buksa
(74) *Attorney, Agent, or Firm* — Harness, Dickey & Pierce, P.L.C.

(57) ABSTRACT

The present invention relates to a method for synchronizing microrobot operation control and position recognition using a dual hybrid electromagnet module, and specifically, precise driving of a microrobot and position recognition of the microrobot may be synchronized by using an electromagnetic field system in which a dual hybrid electromagnet module comprising a permanent magnet and an electromagnet is used for microrobot control so as to enable reducing the number of electromagnets that are used and thus enable reducing power consumption and the amount of heat generated from the electromagnet module. Thus, the present invention may be used for various medical procedures and surgeries using a microrobot.

7 Claims, 16 Drawing Sheets

(56) References Cited

FOREIGN PATENT DOCUMENTS

| | | | |
|---|---|---|---|
| KR | 10-2019-0043778 | A | 4/2019 |
| KR | 10-2022-0064740 | A | 5/2022 |
| KR | 10-2022-0109820 | A | 8/2022 |

OTHER PUBLICATIONS

International Search Report from corresponding PCT Application No. PCT/KR2023/012319, dated Dec. 5, 2023.

Liu, S-L., et al.; "Three-Dimensional Localization of a Robotic Capsule Endoscope Using Magnetoquasistatic Field", IEEE Access, vol. 8, 2020, pp. 1-11.

* cited by examiner

Dual hybrid electromagnet

METHOD FOR SYNCHRONIZING MICROROBOT OPERATION CONTROL AND POSITION RECOGNITION USING DUAL HYBRID ELECTROMAGNET MODULE

CROSS-REFERENCE TO RELATED APPLICATIONS

This application is a national phase application of PCT Application No. PCT/KR2023/012319, filed on Aug. 21, 2023, which claims priority to Korean Patent Application No. 10-2022-0106039, filed on Aug. 24, 2022. The entire disclosures of the applications identified in this paragraph are incorporated herein by reference.

TECHNICAL FIELD

The present disclosure was supported by the Ministry of Health and Welfare under Project No. RS-2023-00302146, the research management agency of the above project is Korea Health Industry Development Institute, the research project title is "Development of Technologies for Advanced Common-Base Modules for Medical Microrobots and Medical Product Commercialization", the research task title is "Development of Technology for Advanced Electromagnetic Actuation Integrated Module for Autonomous Targeting of Medical Microrobots", the host institution is Korea Institute of Medical Microrobotics Institute, and the research period is from Aug. 1, 2023 to Dec. 31, 2027.

The present disclosure relates to a method for synchronizing motion control and position recognition of a microrobot by using a dual hybrid electromagnet module and, more particularly, to a method for synchronizing motion control and position recognition of a microrobot in real time, applicable to a prolonged surgery using a microrobot, by using a dual hybrid electromagnet module in which the number of electromagnets included in the electromagnet module is reduced, thereby decreasing power consumption and the amount of heat generated from the electromagnet module.

BACKGROUND ART

Electromagnetic field devices for driving a microrobot in the human body from outside the human body are being developed. Depending on the purpose of the medical procedure in the human body, wired or wireless microrobots are utilized, and technologies to drive a microrobot by controlling the direction and magnitude of a magnetic field through an electromagnetic field device are known or under development. Specifically, an electromagnetic field device, which includes multiple electromagnets/permanent magnets arranged in consideration of a disease site in the human body and the movement characteristics of a microrobot and has a fixed or mobile system structure, is being developed.

Previously developed electromagnetic field driving devices are inefficient from various operational perspectives because the large number of electromagnets used increases the device size, making installation and operation of the device inefficient in a procedure space, and the increase in the number of power supplies due to the increase in the number of electromagnets increases power consumption.

Additionally, in the case of a magnetic field driving device using a permanent magnet, the number of magnets used is small, but there are limitations in controlling a microrobot. In addition, the permanent magnet has a constant magnetization value, and the robot is driven by changing the distance between the robot and the magnet and switching the direction of the magnet, resulting in limitations in control performance. Although a motor is used to secure a control space for the permanent magnet, there are difficulties in real-time magnetic field control due to the time difference in motor movement. In addition, the conventional method for controlling a robot by changing the gradient magnetic field and uniform magnetic field in space has the limitation that it is difficult to concentrate the robot at a desired position without position information.

Furthermore, the conventional microrobot control method controls a capsule endoscope by changing a gradient magnetic field and a uniform magnetic field in space, so it is difficult to concentrate the capsule endoscope at a desired position without the position information of the capsule endoscope.

Furthermore, the conventional microrobot position recognition methods may include an RF signal-based position recognition method and a Hall sensor-based position recognition method, integrated with a microrobot driving device, and a position recognition method using a position recognition device configured separately from the driving device.

Among the methods, the RF signal-based method may cause errors due to differences in the radiation characteristics of the RF antenna in a capsule endoscope and differences in a patient's body penetration characteristics, and the hall sensor-based method may cause errors because the magnetic field measurement efficiency of a Hall sensor decreases significantly as the distance between the Hall sensor and a capsule endoscope increases. Therefore, there is a problem that the errors are significant depending on environmental factors. In addition, using a position recognition device that is configured separately from an electromagnetic field driving device requires individual technology for each device, and necessitates the development of new technology to synchronize the technologies, and increases the size of the entire device.

In order to solve the above-described problems of the prior art, the present inventors have completed the present disclosure which is a method for synchronizing motion control and position recognition of a microrobot by using a dual hybrid electromagnet module of the present disclosure.

DISCLOSURE OF INVENTION

Technical Problem

Accordingly, the present inventors have confirmed that the method of synchronizing motion control and position recognition of a microrobot, according to the present disclosure, can synchronize accurate control of the microrobot and position recognition of the microrobot.

Accordingly, an aspect of the present disclosure is to provide a method for synchronizing motion control and position recognition of a microrobot.

Solution to Problem

The present disclosure relates to a method for synchronizing motion control and position recognition of a microrobot by using a dual hybrid electromagnet module. Precise driving of a microrobot and position recognition of the microrobot may be synchronized by using the method according to the present disclosure.

Hereinafter, the present disclosure will be described in more detail.

An aspect of the present disclosure relates to a method for synchronizing motion control and position recognition of a microrobot, performed using an electromagnetic field system in which electromagnet modules are arranged such that central axes of the electromagnet modules intersect to form an intersection point. The method for synchronizing motion control and position recognition of a microrobot includes: a current application step of independently applying a current from a power supplier to each of a first hybrid electromagnet module and a second hybrid electromagnet module; a steering step of controlling a motion of the microrobot by using a direct current magnetic field generated from the first hybrid electromagnet module and the second hybrid electromagnet module; a reflected signal reception step of receiving, via a communication module, a reflected signal generated by an Rx module included in the microrobot by using an alternating current magnetic field generated from the first hybrid electromagnet module and the second hybrid electromagnet module; and a position recognition step of recognizing a position of the microrobot by using the reflected signal.

In the present disclosure, the electromagnetic field system may include: a first hybrid electromagnet module; and a second hybrid electromagnet module, the first hybrid electromagnet module may include a first magnetic body including a first permanent magnet and a first electromagnet including a first magnetic core and a first wire wound on the first magnetic core, the second hybrid electromagnet module may include a second magnetic body including a second permanent magnet, and a second electromagnet including a second magnetic core and a second wire wound on the second magnetic core, and the first hybrid electromagnet module and the second hybrid electromagnet module may be arranged such that the central axis of the first hybrid electromagnet module and the central axis of the second hybrid electromagnet module intersect to form an intersection point.

In an embodiment of the present disclosure, the first electromagnet or the second electromagnet may be at least one type of coil selected from a solenoid coil, a circular coil, a square coil, a Maxwell coil, a Helmholtz coil, and a saddle coil.

The term "circular coil" in the present specification may be interpreted as a circular electromagnet, and the circular electromagnet refers to a ring-shaped magnet, i.e., a magnet without ends in which the effect of demagnetizing force at the ends does not appear.

In an embodiment of the present disclosure, the electromagnetic field system may further include a frame unit configured to connect the first hybrid electromagnet module to the second hybrid electromagnet module.

In an embodiment of the present disclosure, at least one of the first permanent magnet and the second permanent magnet may include a hollow center portion.

In an embodiment of the present disclosure, with respect to the intersection point at which the respective central axes of the first hybrid electromagnet module and the second hybrid electromagnet module intersect, the first electromagnet may be disposed farther from the intersection point than the first magnetic body in the first hybrid electromagnet module, and with respect to the intersection point at which the respective central axes of the first hybrid electromagnet module and the second hybrid electromagnet module intersect, the second electromagnet may be disposed farther from the intersection point than the second magnetic body in the second hybrid electromagnet module.

The term "intersection point" in the present specification refers to a virtual point at which a virtual axis passing through the center of the first hybrid electromagnet module meets a virtual axis passing through the center of the second hybrid electromagnet module. Although not limited thereto, the intersection point may be positioned within a region of interest, which is the area where the microrobot is intended to be driven.

Specifically, in the first hybrid electromagnet module or the second hybrid electromagnet module according to the present disclosure, the first electromagnet and the first magnetic body or the second electromagnet and the second magnetic body may be arranged in sequence from the intersection point.

When the electromagnets are placed closer to the intersection point, the electromagnet which is a device for controlling a main microrobot are placed at the bottom, thereby improving the performance of controlling the motion of the microrobot and precisely manipulating the microrobot even with a small change in current.

In an embodiment of the present disclosure, the first hybrid electromagnet module and the second hybrid electromagnet module may be arranged such that the central axis of the first hybrid electromagnet module and the central axis of the second hybrid electromagnet module form an angle of any one of 1 to 90, 10 to 80, 10 to 70, 10 to 60, 10 to 50, 20 to 80, 20 to 70, 20 to 60, 20 to 50, or 20 to 40 degrees. For example, the first hybrid electromagnet module and the second hybrid electromagnet module may be arranged to form an angle of 30 degrees. However, the present disclosure is not limited thereto.

In an embodiment of the present disclosure, the magnetization direction of the first magnetic body and the first electromagnet may be parallel to the central axis of the first hybrid electromagnet module, and the magnetization direction of the second magnetic body and the second electromagnet may be parallel to the central axis of the second hybrid electromagnet module. Thus, by adjusting the direction and amount of current applied to each hybrid electromagnet module, the user can control each hybrid electromagnet module to have a magnetic field direction toward the intersection point or set the magnetic field direction in a direction opposite to the intersection point.

In an embodiment of the present disclosure, the first magnetic body and the second magnetic body may be arranged such that the magnetic field directions of the first magnetic body and the second magnetic body with respect to the intersection point are opposite to each other.

In an embodiment of the present disclosure, the first hybrid electromagnet module and the second hybrid electromagnet module may be arranged such that the central axis of the first hybrid electromagnet module and the central axis of the second hybrid electromagnet module form 30 degrees, and the magnetic field directions of the first magnetic body and the second magnetic body may be arranged in opposite directions with respect to the intersection point. When the first hybrid electromagnet module and the second hybrid electromagnet module are arranged as described above, the user can freely adjust the direction of the magnetic field within the region of interest (ROI) from −90 to 60 degrees by applying no current to the electromagnet in each hybrid electromagnet module, or by adjusting the direction and strength of current applied to the electromagnet (see FIG. 4, FIGS. 5A to 5D).

In an embodiment of the present disclosure, at least one of the first electromagnet and the second electromagnet may include a solenoid coil.

In an embodiment of the present disclosure, the electromagnetic field system may further include a controller configured to control the first hybrid electromagnet module and the second hybrid electromagnet module.

In an embodiment of the present disclosure, the electromagnetic field system may further include a power supplier configured to apply a current to the first hybrid electromagnet module and the second hybrid electromagnet module.

In an embodiment of the present disclosure, the electromagnetic field system may further include a cooler.

In an embodiment of the present disclosure, the frame unit may include a shielding material.

In an embodiment of the present disclosure, the electromagnetic field system may further include an arm unit configured to move the position of the first hybrid electromagnet module and the second hybrid electromagnet module.

In an embodiment of the present disclosure, the electromagnetic field system may further include a bed.

In an embodiment of the present disclosure, the first permanent magnet and the second permanent magnet may be square or cylindrical.

In an embodiment of the present disclosure, the electromagnetic field system may further include the frame unit configured to connect the first hybrid electromagnet module and the second hybrid electromagnet module to each other.

In an embodiment of the present disclosure, at least one of the first permanent magnet and the second permanent magnet may include a hollow center portion.

In an embodiment of the present disclosure, with respect to the intersection point at which the respective central axes of the first hybrid electromagnet module and the second hybrid electromagnet module intersect, the first electromagnet may be disposed farther from the intersection point than the first magnetic body in the first hybrid electromagnet module, and with respect to the intersection point at which the respective central axes of the first hybrid electromagnet module and the second hybrid electromagnet module intersect, the second electromagnet may be disposed farther from the intersection point than the second magnetic body in the second hybrid electromagnet module.

In an embodiment of the present disclosure, the first hybrid electromagnet module and the second hybrid electromagnet module may be arranged such that the central axis of the first hybrid electromagnet module and the central axis of the second hybrid electromagnet module form an angle of any one of 1 to 90, 10 to 80, 10 to 70, 10 to 60, 10 to 50, 20 to 80, 20 to 70, 20 to 60, 20 to 50, or 20 to 40 degrees. For example, the first hybrid electromagnet module and the second hybrid electromagnet module may be arranged to form an angle of 30 degrees. However, the present disclosure is not limited thereto.

In an embodiment of the present disclosure, the first magnetic body and the second magnetic body may be arranged such that the magnetic field directions of the first magnetic body and the second magnetic body with respect to the intersection point are opposite to each other.

In an embodiment of the present disclosure, the electromagnetic field system may further include a controller configured to control the first hybrid electromagnet module and the second hybrid electromagnet module.

In an embodiment of the present disclosure, the electromagnetic field system may further include a power supplier configured to apply a current to the first hybrid electromagnet module and the second hybrid electromagnet module.

In an embodiment of the present disclosure, the electromagnetic field system may further include a cooler.

In an embodiment of the present disclosure, the frame unit may include a shielding material.

In an embodiment of the present disclosure, the electromagnetic field system may further include an arm unit configured to move the position of the first hybrid electromagnet module and the second hybrid electromagnet module.

In an embodiment of the present disclosure, the electromagnetic field system may further include a bed.

In an embodiment of the present disclosure, the first permanent magnet and the second permanent magnet may be square or cylindrical.

In the present disclosure, the microrobot is a type of body-inserted medical device, and may be classified into a mechanical/electronic microrobot, which includes a permanent magnet or a soft magnetic body as a millimeter-scale magnetic body, such as a vascular robot or an active capsule endoscope, and a polymeric/cell-based microrobot, which includes magnetic nanoparticles as a micro/nanoscale magnetic body, such as a microcarrier for DDS, a micro-scaffold for cell therapeutics delivery, a nanorobot, or a macrophage robot, and may include other types of microrobots.

In the present disclosure, the microrobot may include a camera module, a driving unit, a position information provision unit, a robot controller, a data transceiver, and a battery unit.

In the present disclosure, the driving unit may be a third magnetic body miniaturized to the size of the microrobot.

In the present disclosure, the third magnetic body is a millimeter-scale magnetic body that may be a permanent magnet or a soft magnetic body, but is not limited to thereto.

In the present disclosure, the position information provision unit may include one Rx coil, two Rx coils, or three Rx coils to generate a reflected signal under magnetic field conditions generated by the electromagnet.

In an embodiment of the present disclosure, the position information provision unit may be a three-axis Rx module including three Rx coils.

In an embodiment of the present disclosure, the three-axis Rx module may be disposed to surround the third magnetic body in the direction of the lengthwise major axis (e.g., the x-axis) of the microrobot, the direction of the widthwise minor axis (e.g., the y-axis) of the microrobot perpendicular to the major axis, and the direction of an axis (e.g., the z-axis) perpendicular to both the lengthwise and widthwise axes of the microrobot.

In the present disclosure, the data transceiver may be one or more types selected from the group consisting of an RF transceiving coil or Bluetooth, but is not limited thereto.

In the present disclosure, the data transceiver may transmit image information acquired by the camera module from the microrobot to the electromagnetic field system or a separately provided display device, but the present disclosure is not limited thereto.

In the present disclosure, the data transceiver part may transmit electromotive force (EMF) information generated by the third magnetic body of the microrobot to the controller of the electromagnetic field system, but the present disclosure is not limited thereto.

In the present disclosure, the battery unit may supply power to the camera module and the data transceiver.

In the present disclosure, the microrobot may additionally include a treatment unit.

In the present disclosure, in the current application step, a current may be independently applied to each of the first hybrid electromagnet module and the second hybrid electromagnet module from the power supplier.

In the present disclosure, the current may be a direct current-alternating current integrated current (DC-AC) including a direct current (DC) and an alternating current (AC).

In the present disclosure, in the steering step, the motion of the microrobot may be controlled using a direct current magnetic field generated by the first hybrid electromagnet module and the second hybrid electromagnet module.

In the present disclosure, the third magnetic body of the microrobot may respond to the direct current magnetic field generated by the first hybrid electromagnet module and the second hybrid electromagnet module, so that an attractive or repulsive force acts on the third magnetic body under the magnetic field, thereby controlling the motion of the microrobot.

In the present disclosure, in the reflected signal reception step, a reflected signal generated by the Rx module included in the microrobot by using an alternating current magnetic field generated by the first hybrid electromagnet module and the second hybrid electromagnet module may be received via the communication module.

In the present disclosure, the reflected signal reception step may be performed before the steering step, but the present disclosure is not limited thereto.

In the present disclosure, in the position recognition step, the position of the microrobot may be recognized using the reflected signal.

In the present disclosure, the position recognition step may include: an extraction step of separating/extracting a frequency-specific signal from a mixed signal; and a conversion step of converting the frequency-specific signal into microrobot position information by using a 6 DoF inverse model.

In an embodiment of the present disclosure, in the extraction step, the frequency-specific signal may be separated/extracted using a fast Fourier transform (FFT) algorithm.

In an embodiment of the present disclosure, the conversion step may further include a display step of displaying the microrobot position information to the user via the separately provided display device, but the present disclosure is not limited thereto.

In an embodiment of the present disclosure, the display step may further include a manipulation step of receiving driving information of the microrobot from a user via a separately provided haptic device, but the present disclosure is not limited thereto.

Advantageous Effects of Invention

The present disclosure relates to a method for synchronizing motion control and position recognition of a microrobot by using a dual hybrid electromagnet module, and specifically, enables precise driving of a microrobot and position recognition of the microrobot to be synchronized using an electromagnetic field system in which a dual hybrid electromagnet module including a permanent magnet and an electromagnet is used for microrobot control, thereby reducing the number of electromagnets used and thus reducing power consumption and the amount of heat generated from the electromagnet module. Thus, the present disclosure may be used for various medical procedures and surgeries using a microrobot.

BEST MODE FOR CARRYING OUT THE INVENTION

Figure 1:
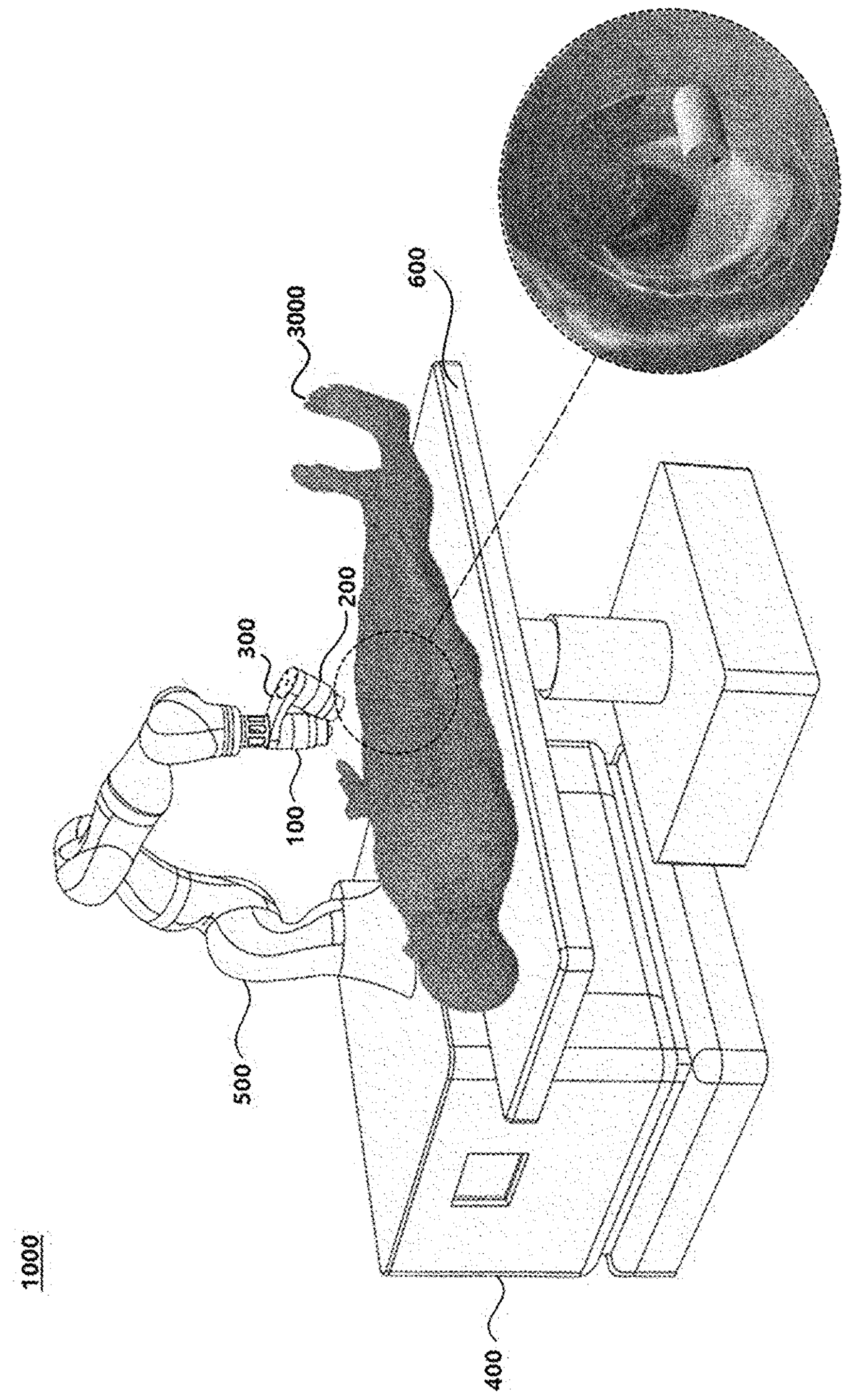
FIG. 1 illustrates an electromagnetic field system used in the present disclosure.

A method for synchronizing motion control and position recognition of a microrobot, performed using an electromagnetic field system in which electromagnet modules are arranged such that the central axes of the electromagnet modules intersect to form an intersection point, includes:

- a current application step of independently applying a current from a power supplier to each of a first hybrid electromagnet module and a second hybrid electromagnet module;
- a steering step of controlling the motion of the microrobot by using a direct current magnetic field generated from the first hybrid electromagnet module and the second hybrid electromagnet module;
- a reflected signal reception step of receiving, via a communication module, a reflected signal generated by an Rx module included in the microrobot by using an alternating current magnetic field generated from the first hybrid electromagnet module and the second hybrid electromagnet module; and
- a position recognition step of recognizing a position of the microrobot by using the reflected signal.

MODE FOR CARRYING OUT THE INVENTION

The terms used in the present disclosure are used only to describe specific embodiments and are not intended to limit the invention. Singular expressions include plural expressions unless the context clearly indicates otherwise. In the present application, the terms "include", "have", etc. are intended to designate the presence of the features, numbers, steps, operations, elements, parts, or combinations thereof described in the description of the invention, and should be understood as not excluding the possibility of the presence or addition of one or more other features, numbers, steps, operations, elements, parts, or combinations thereof.

The terms "first", "second", and the like may be used to describe various elements, but the elements should not be limited by such terms. The terms are used only for the purpose of distinguishing one element from another element. For example, a first element may be referred to as a second element, and similarly, a second element may be referred to as a first element, without departing from the scope of the present disclosure.

Unless otherwise defined, all terms used herein, including technical or scientific terms, have the same meaning as those commonly understood by a person skilled in the art to which the present disclosure belongs. Terms, as defined in commonly used dictionaries, should be interpreted to have the meanings equal to the contextual meanings in the relevant art, and should not be interpreted ideally or excessively unless explicitly defined by the present disclosure.

In interpreting an element, it is interpreted to include an error range, even in the absence of separate explicit description. When a temporal relationship is described, for example, when the temporal order is described with the terms "after", "following", "next to", "before", etc., this includes a non-continuous relation unless the term "immediately" or "directly" is used.

Hereinafter, the technical configuration of the present disclosure will be described in detail with reference to the accompanying drawings.

FIG. 1 illustrates an electromagnetic field system 1000 used in the present disclosure.

Referring to FIG. 1, the electromagnetic field system 1000 may include a first hybrid electromagnet module 100, a second hybrid electromagnet module 200, a frame 300, a body unit 400, an arm 500, and a bed 600.

The first hybrid electromagnet module (100) may be connected to the second hybrid electromagnet module 200 through the frame 300, and at least one of the first hybrid electromagnet module 100 or the second hybrid electromagnet module 200 connected through the frame 300 may be disposed to be connected to one end of the arm 500.

The first hybrid electromagnet module 100 and the second hybrid electromagnet module 200 may receive power from a power supplier included in the body unit 400. The first hybrid electromagnet module 100 or the second hybrid electromagnet module 200 may receive power from the power supplier via a wire disposed inside or outside the arm 500. In this case, the frame 300 may include a wire therein, allowing the power supplied from the power supplier to pass through the arm 500 and be supplied to the second hybrid electromagnet module 200 via the frame 300.

Furthermore, the first hybrid electromagnet module 100 and the second hybrid electromagnet module 200 may receive power from power supplier via wires directly connected to each of the hybrid electromagnet modules 100 and 200.

The first hybrid electromagnet module 100 and the second hybrid electromagnet module 200 may be disposed to face the bed 600, and, when a subject is positioned on the bed 600, the modules may be driven to control a microrobot within a region of interest located above the bed 600.

The body unit 400 may include the power supplier.

The power supplier may apply a current to the first hybrid electromagnet module 100 and the second hybrid electromagnet module 200 via the arm or directly in the body unit 400. As will be described later, the electromagnetic field system 1000 uses dual hybrid electromagnet modules 100 and 200, and thus consumes less power than a conventional electromagnetic field system including only electromagnets. Therefore, the power supplier may efficiently control the microrobot by supplying only a small amount of current to each of the hybrid electromagnet modules 100 and 200.

The body unit 400 may include a cooler (not shown), and the cooler may cool the first hybrid electromagnet module 100 and the second hybrid electromagnet module 200.

The arm 500 may be disposed on the top of the body unit 400. The arm 500 may move the position of the first hybrid electromagnet module 100 and the second hybrid electromagnet module 200. Thus, a user can move each of the hybrid electromagnet modules 100 and 200 to apply a magnetic field to the region of interest through the electromagnetic field system 1000, thereby controlling the motion and recognizing the position of a microrobot located in a subject 3000 as a patient by. Detailed configurations of the microrobot and a method for motion control and position recognition thereof are described in detail in FIGS. 9 to 13.

Figure 2:
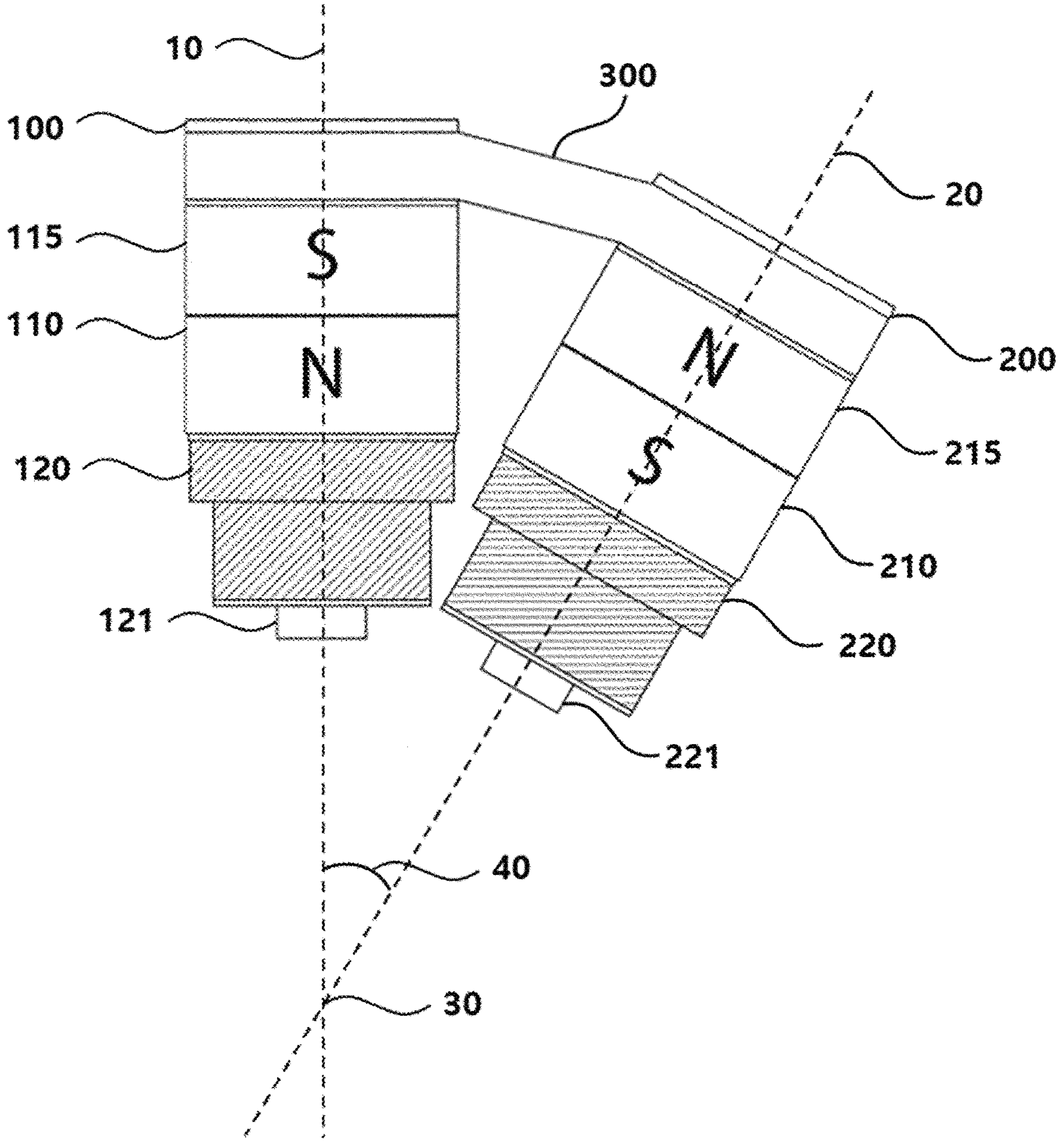
FIG. 2 illustrates a dual hybrid electromagnet module used in the present disclosure.
Figure 3:
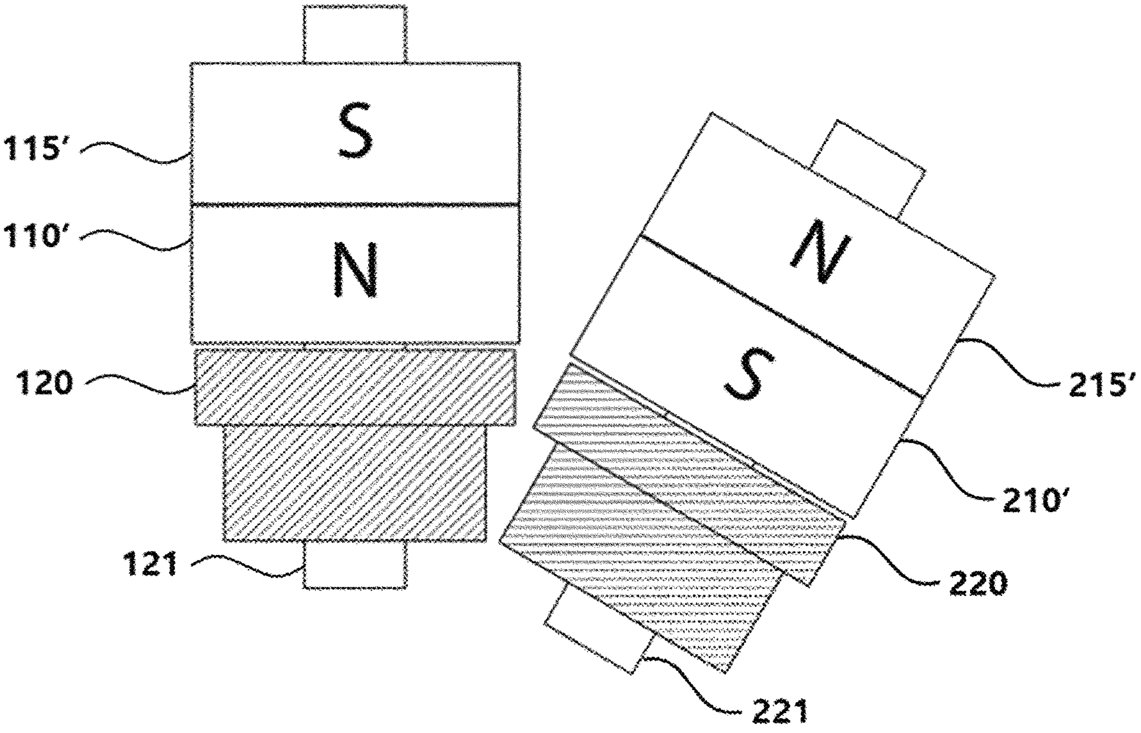
FIG. 3 illustrates a dual hybrid electromagnet module used in the present disclosure.

FIG. 2 illustrates a dual hybrid electromagnet module according to an embodiment of the present disclosure. FIG. 3 illustrates a dual hybrid electromagnet module according to another embodiment of the present disclosure.

Referring to FIGS. 2 and 3, the first hybrid electromagnet module 100 may include a first magnetic body 110 and a first electromagnet 120, and the second hybrid electromagnet module 200 may include a second magnetic body 210 and a second electromagnet 220.

Meanwhile, the first hybrid electromagnet module 100 and the second hybrid electromagnet module 200 may be arranged such that the central axis 10 of the first hybrid electromagnet module and the central axis 20 of the second hybrid electromagnet module intersect to form an intersection point 30. When the center axes of the hybrid electromagnet modules are arranged to form the intersection point 30, a magnetic field generated by each hybrid electromagnet module may be concentrated at the intersection point.

The central axis 10 of the first hybrid electromagnet module and the central axis 20 of the second hybrid electromagnet module may be arranged to form a predetermined angle 30. The angle formed by the two central axes 10 and 20 may be any one of 1 to 90, 10 to 80, 10 to 70, 10 to 60, 10 to 50, 20 to 80, 20 to 70, 20 to 60, 20 to 50, or 20 to 40 degrees, and may, for example, be 30 degrees, but is not limited thereto.

The first magnetic body 110 may include a first permanent magnet 115, and the second magnetic body 210 may include a second permanent magnet 215.

The first permanent magnet or the second permanent magnet may be at least one of a neodymium magnet, a ferrite magnet, an alnico magnet, a samarium cobalt magnet, and a rubber magnet, or a combination thereof, and may be, for example, a neodymium magnet, but is not limited thereto.

In this case, the first magnetic body 110 may be disposed in the first hybrid electromagnet module 100 such that the magnetization direction is parallel to the central axis 10 of the first hybrid electromagnet module, and the second magnetic body 210 may be disposed in the second hybrid electromagnet module 200 such that the magnetization direction is parallel to the central axis 20 of the second hybrid electromagnet module.

The first magnetic body 110 and the second magnetic body 210 may be arranged such that the magnetic field directions of the first magnetic body 110 and the second magnetic body 210 are opposite to each other with respect to the intersection point 30. For example, as illustrated in FIGS. 2 and 3, in the first hybrid electromagnet module 110, the S pole of the first permanent magnet 115 may be disposed adjacent to the frame 300 and the N pole may be disposed adjacent to the first electromagnet 120, and in the second hybrid electromagnet module 200, the S pole of the second permanent magnet 215 may be disposed adjacent to the second electromagnet 220 and the N pole may be disposed adjacent to the frame 300.

In addition, when the first magnetic body 110 and the second magnetic body 210 are arranged such that the magnetic field directions of the first magnetic body 110 and the second magnetic body 210 are opposite to each other with respect to the intersection point 30 as described above, the direction of a magnetic field in the region of interest (ROI) may be set to a specific direction by using only the permanent magnets, even if no current is applied to the first electromagnet 120 and the second electromagnet 220.

At least one of the first permanent magnet 110 and the second permanent magnet 210 may include hollow center portion. For example, as shown in FIG. 3, both a first permanent magnet 110' and a second permanent magnet 210' may include a hollow center portion.

The first electromagnet 120 may include a first magnetic core 121 and a first wire wound on the first magnetic core.

The second electromagnet 220 may include a second magnetic core 221 and a second wire wound on the second magnetic core.

Each of the first electromagnet 120 and the second electromagnet 220 may be at least one type of coil selected from a solenoid coil, a circular coil, a square coil, a Maxwell coil, a Helmholtz coil, and a saddle coil, and may be, for example, a solenoid coil.

The first wire or the second wire may be enameled wire, copper, enameled copper wire, enameled aluminum wire.

The frame 300 may connect the first hybrid electromagnet module 100 and the second hybrid electromagnet module 200 to each other.

The frame 300 may include a shielding material, and when the shielding material is included in the frame 300, it is possible to suppress interference between magnetic fields generated by the first hybrid electromagnet module 100 and the second hybrid electromagnet module 200.

In the first hybrid electromagnet module 100 and the second hybrid electromagnet module 200, with respect to the intersection point 30, the first electromagnet 120 may be disposed farther from the intersection point than the first magnetic body 110 in the first hybrid electromagnet module 100, and the second electromagnet 220 may be disposed farther from the intersection point than the second magnetic body 210 in the second hybrid electromagnet module 200.

Figure 4:
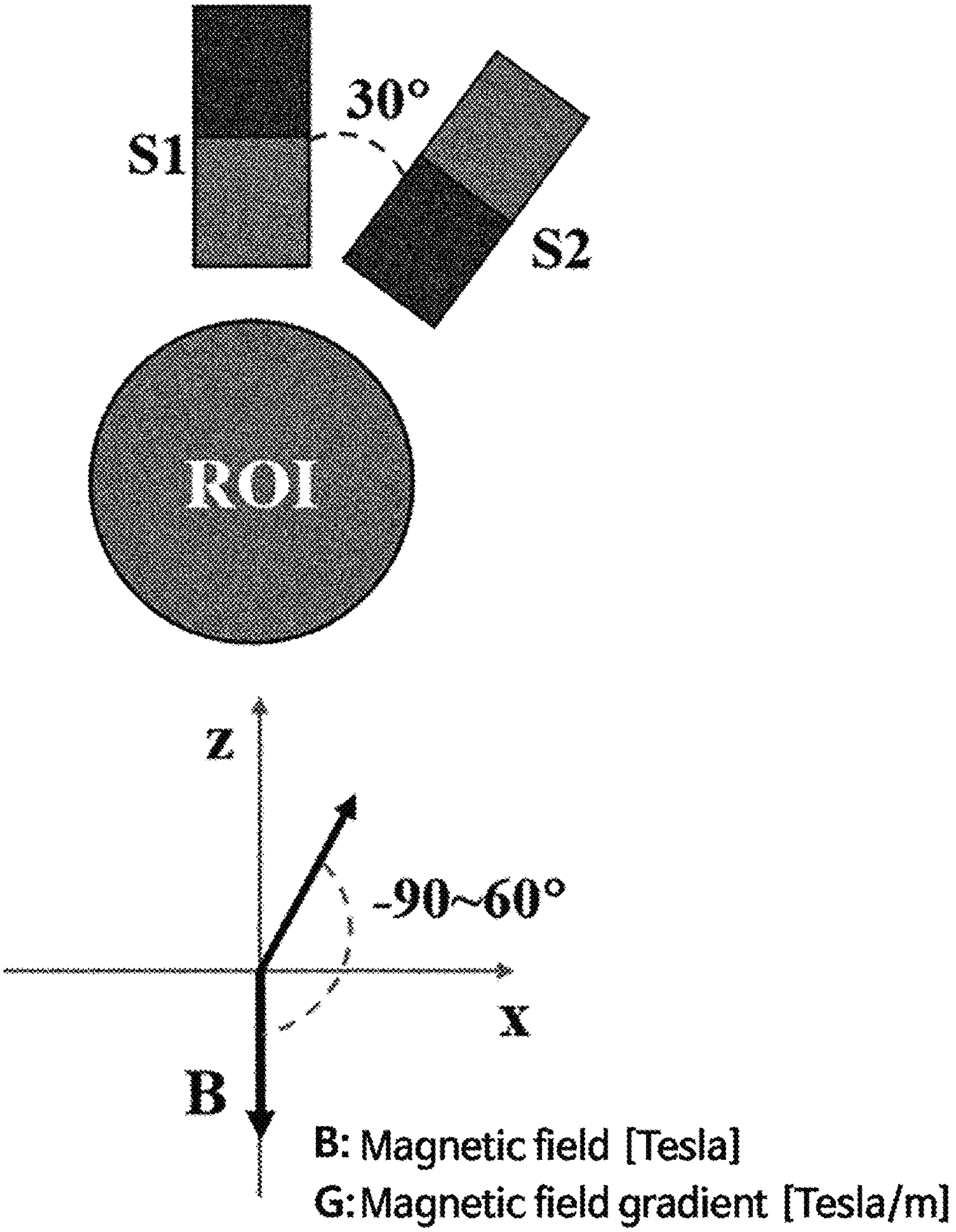
FIG. 4 illustrates a magnetic field direction control range within a region of interest (ROI) of an electromagnetic field system used in the present disclosure.

FIG. 4 illustrates a magnetic field direction control range within a region of interest (ROI) of an electromagnetic field system used in the present disclosure. FIGS. 5A to 5D illustrate the magnetic field direction of each hybrid electromagnet module according to applied current values in an electromagnetic field system.

Referring to FIGS. 4 and 5A to 5D, the electromagnetic field device according to the present disclosure may have a magnetic field direction control range of −90 to 60 degrees in the region of interest when the first hybrid electromagnet module and the second hybrid electromagnet module are arranged at a 30-degree angle.

Figure 5A:
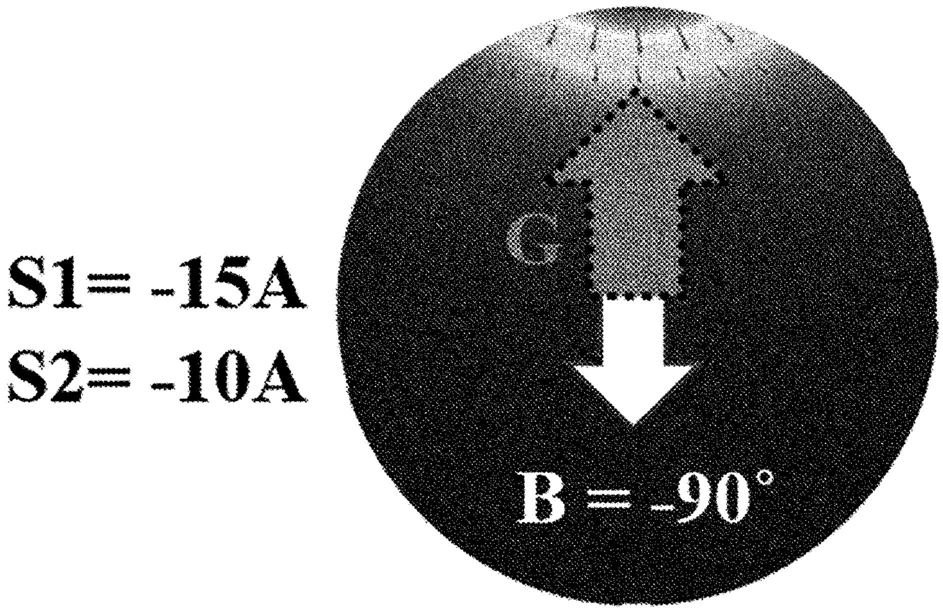
FIGS. 5A, 5B, 5C and 5D illustrate the magnetic field direction of each hybrid electromagnet module according to applied current values in an electromagnetic field system used in the present disclosure.

Specifically, referring to FIG. 5A, when a current of −15 A is applied to a first hybrid electromagnet module S1 and a current of −10 A is applied to a second hybrid electromagnet module S2, the direction of a magnetic field in the region of interest may be controlled to be −90 degrees. In this case, the first hybrid electromagnet module and the second hybrid electromagnet module form a magnetic field regardless of the application of current, and magnetic fields of a first permanent magnet and a second permanent magnet overlap to form a magnetic field in the 0-degree direction. Then, when the respective currents are applied to the first electromagnet and the second electromagnet, and magnetic fields all overlap the magnetic fields formed by the permanent magnets, thereby forming a magnetic field in the −90-degree direction.

Figure 5B:
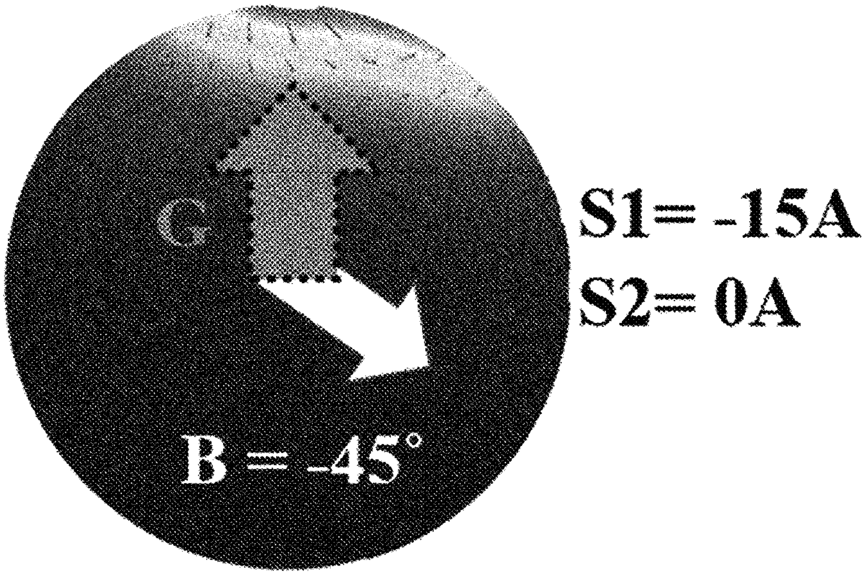
Figure 5C:
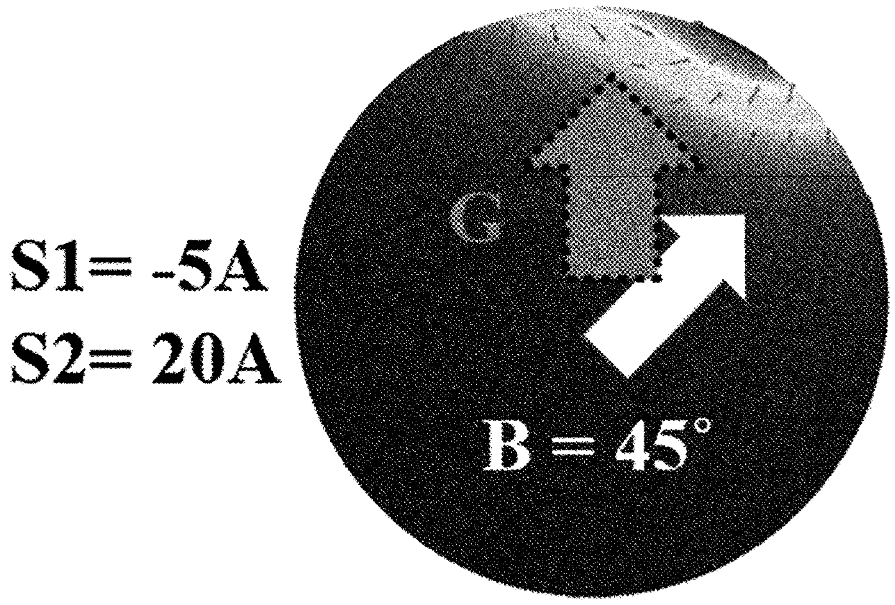
Figure 5D:
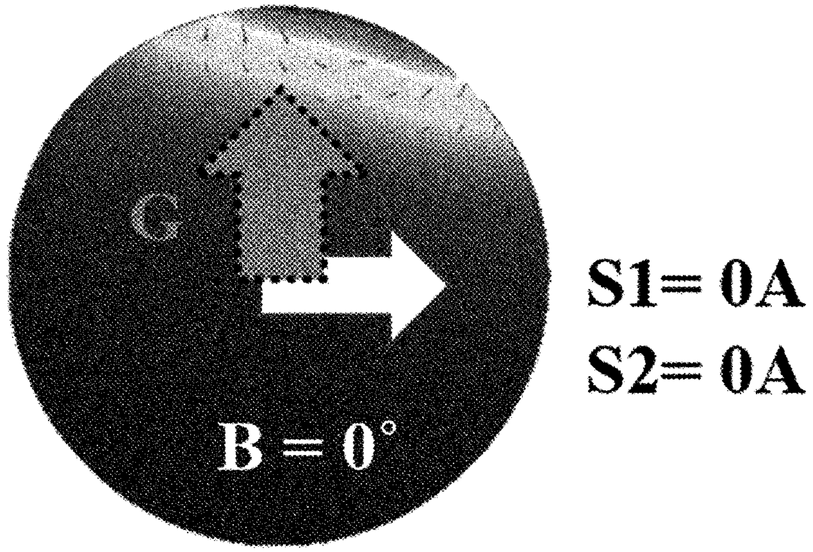

Furthermore, referring to FIG. 5B, when a current of −15 A is applied to the first hybrid electromagnet module and no current is applied to the second hybrid electromagnet module, a magnetic field formed by the first electromagnet may overlap the magnetic fields formed by the first permanent magnet and the second permanent magnet to form a magnetic field in the −45-degree direction.

Referring to 5C, when a current of −5 A is applied to the first hybrid electromagnet module and a current of 20 A is applied to the second hybrid electromagnet module, the magnetic fields generated by the first electromagnet, the second electromagnet, the first permanent magnet, and the second permanent magnet all overlap to form a magnetic field in the 45-degree direction.

Finally, as described above, when a magnetic field is formed with only permanent magnets without applying a current to the first and second electromagnets, it is possible to form a magnetic field in the 0-degree direction depending on the angle (30 degrees) at which the first permanent magnet and the second permanent magnet are arranged.

As described above, in the electromagnetic field system, each hybrid electromagnet module includes a permanent magnet in addition to an electromagnet, and the hybrid electromagnet modules are arranged to form a predetermined angle relative to each other. Thus, it is possible to form a magnetic field in a certain direction without applying a current to the hybrid electromagnet module. Furthermore, by appropriately adjusting the direction and strength of the current applied to each hybrid electromagnet module, it is possible to freely form a magnetic field in the direction of −90 to 60 degrees in the region of interest.

Therefore, the electromagnetic field system may realize a magnetic field system without power consumption and heat generation of the electromagnets. Furthermore, power used by the power supplier is reduced due to the minimization of the number of electromagnets used in the entire system, the system may be driven without reducing the cooling capacity of the cooler or configuring an additional cooling device, and the amount of power consumed and the amount of heat generated by the entire system are minimized, thereby enabling the system to be utilized in procedures or surgeries using microrobots for a long time.

Embodiment 1: Identification of the Driving of a Microrobot in the Electromagnetic Field System Two hybrid electromagnet modules, each including a neodymium permanent magnet and an electromagnet, were fabricated and connected to a frame. After attaching the hybrid electromagnet modules to a robot arm, an experiment to drive a microrobot was conducted.

Each hybrid electromagnet module was controlled by applying or not applying current to the hybrid electromagnet modules. A prototype capsule-type robot was placed in a transparent plastic cylindrical environment and changes in the position of the robot were measured by changing the direction and intensity of current in the hybrid electromagnet modules.

Figure 6:
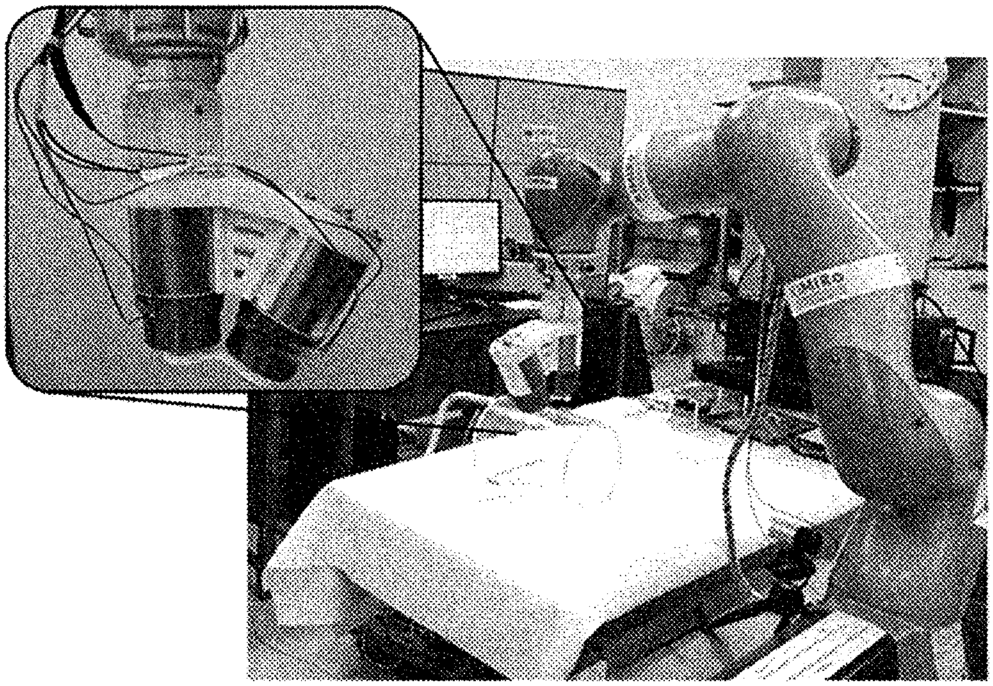
FIG. 6 is a photograph illustrating a prototype of an electromagnetic field system used in the present disclosure.
Figure 7:
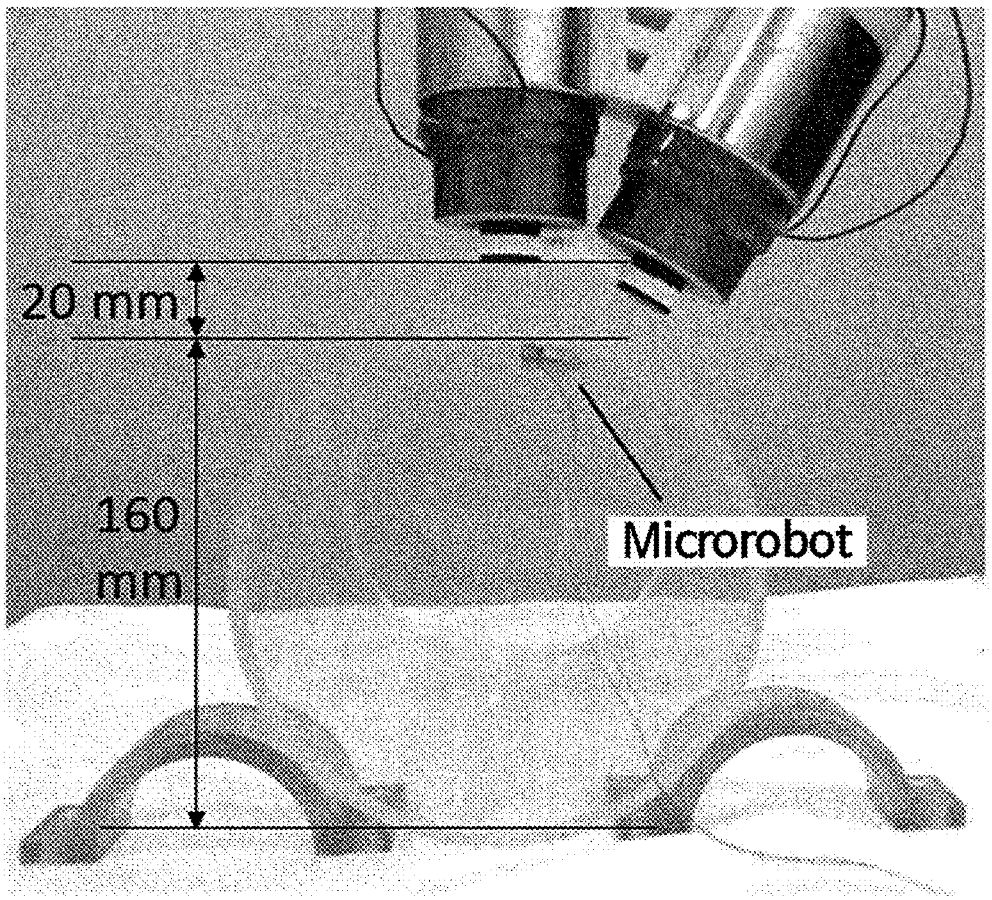
FIG. 7 is a photograph obtained by photographing a scene in which a prototype microrobot of an electromagnetic field system used in the present disclosure is driven.

As shown in FIGS. 6 and 7, as a result of the measurement, it was identified that motions of the five degrees of freedom of the capsule-type robot, i.e., three degrees of freedom in position movement and two degrees of freedom in angular movement, is precisely controlled. In this case, it was also identified that the power consumption of the entire electromagnetic field system is significantly reduced.

Embodiment 2: Identification of the Synchronization of Motion Control and Position Recognition of a Microrobot

2-1. Microrobot

Figure 8:
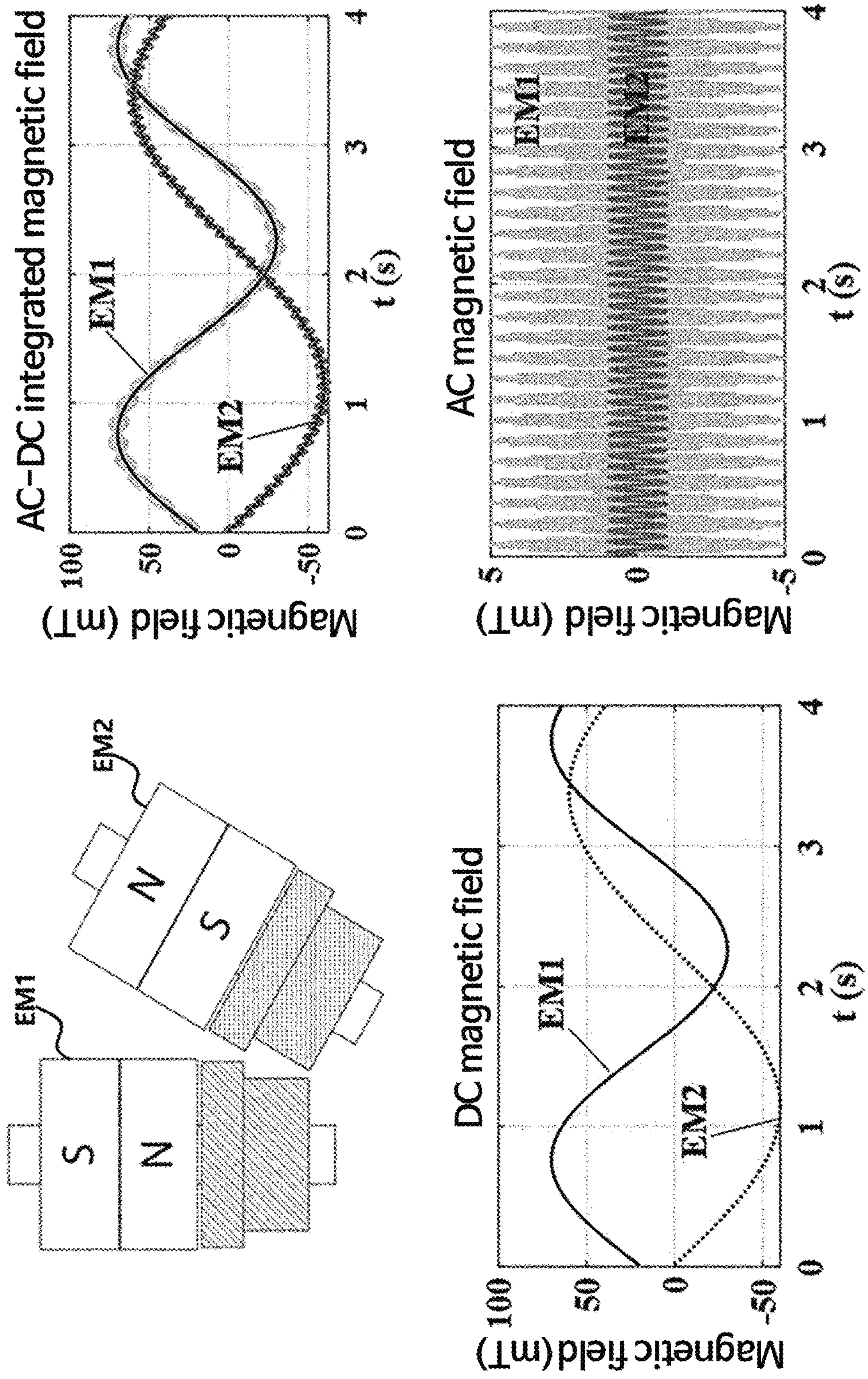
FIG. 8 illustrates a direct current (DC)-alternating current (AC) integrated magnetic field generated by electromagnets EM1 and EM2 of a dual hybrid electromagnet module used in the present disclosure.

FIG. 8 illustrates a DC-AC integrated magnetic field generated by electromagnets EM1 and EM2 of a dual hybrid electromagnet module used in the present disclosure.

Referring to FIG. 8, each of the electromagnets EM1 and EM2 integrates a DC magnetic field for driving a microrobot and an AC magnetic field for position recognition. In this case, each magnetic field may be independently separated, so that the interference therebetween may be ignored in motion control and position recognition of the microrobot. This enables the motion control and position recognition of the microrobot.

Figure 9:
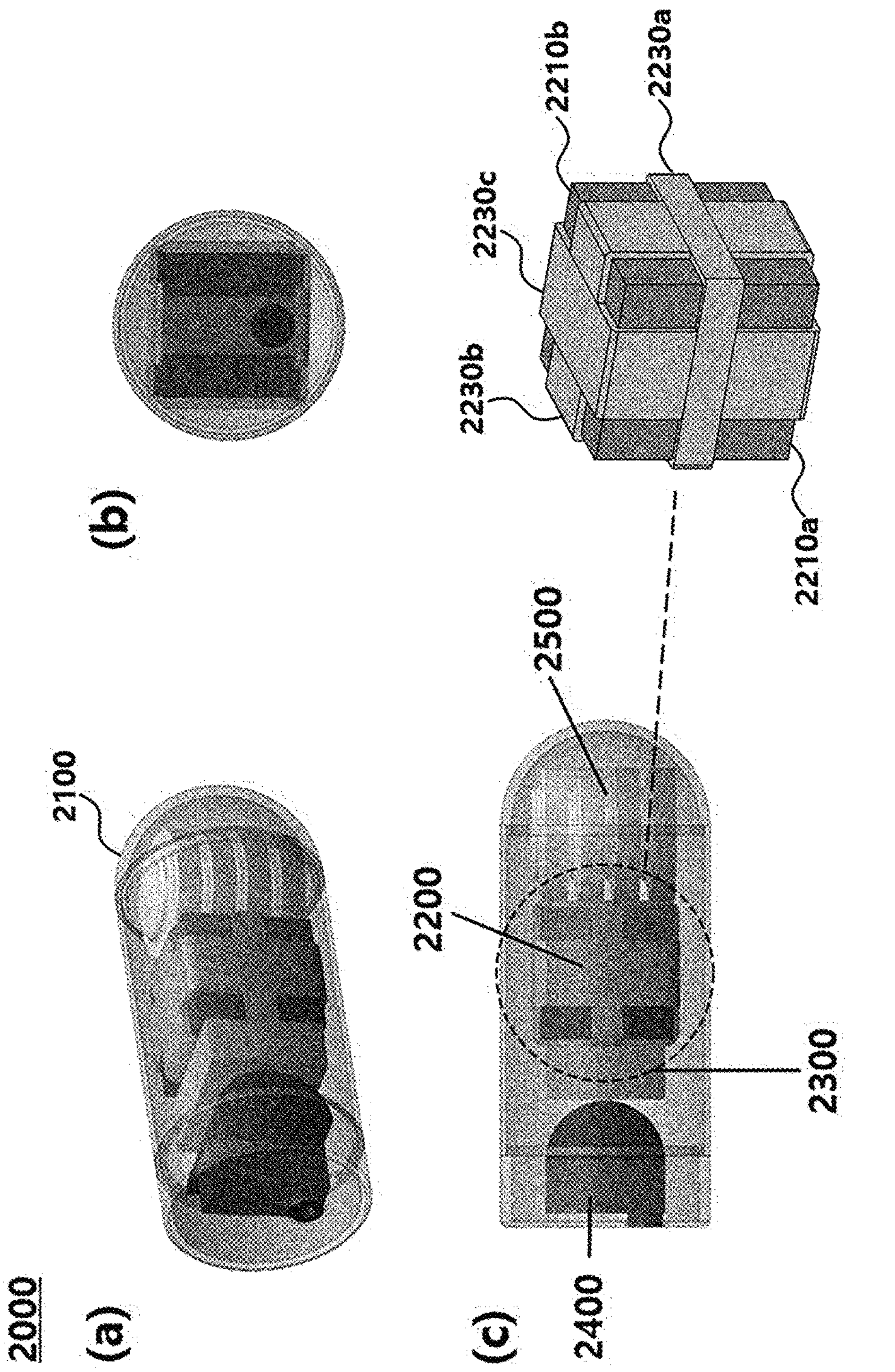
FIG. 9 is an imaginary view showing the exterior and internal elements of a microrobot actively driven by a magnetic field.

FIG. 9 is an imaginary view showing the exterior and internal elements of a microrobot (a capsule endoscope) actively driven by a magnetic field.

Referring to FIG. 9, a microrobot 2000 may be packaged in a capsule-type housing 2100. FIG. 9(A) is a perspective view of the microrobot, but the capsule-type housing itself may be made of a transparent material. The microrobot according to an embodiment of the present disclosure may include a camera module 2400, a data transceiver 2300, a motion control and position information provision unit 2200, and a battery unit 2500. The camera module 2400 may be positioned at one end of the housing, and a lens of the camera module may be positioned on the surface of the housing to capture images of the surroundings of the microrobot. The endoscopic video images captured by the camera module may be transmitted to the electromagnetic field system 1000 of the present disclosure or a separately provided display device (not shown) via the data transceiver 2300. The camera module, the data transceiver, the motion control and position information provision unit, and the battery unit may be sequentially arranged in the capsule-type housing. Furthermore, the camera module, the data transceiver, the position information provision unit, and the battery unit may be connected to each other in a wired or wireless manner to transmit power or signals between each other.

The motion control and position information provision unit 2200 may include a driving unit 2210 and a position information provision unit 2230.

The driving unit 2210 may be a magnetic body miniaturized to be positioned within the capsule-type housing package. The magnetic body of the driving unit may be a millimeter-scale magnetic body and may be a permanent magnet or a soft magnetic body. The magnetic body of the driving unit may be positioned such that an S pole **2210*a* faces the camera module 2400 and an N pole 2210*b* faces the battery unit 2500. The above-described directionality of the magnetic body may determine the directionality of driving of the microrobot 2000 by the electromagnetic field system 1000**. When the polarity direction of the magnetic body is reversed, the directionality of driving of the microrobot may also be reversed.

The position information provision unit 2230 may be disposed to surround the magnetic body 2210 of the driving unit. The position information provision unit may be a three-axis Rx module including three Rx coils. The three-axis Rx module may include a first Rx coil **2230*a* surrounding the magnetic body of the driving unit in the direction of the lengthwise major axis of the microrobot (e.g., an axis from the camera unit to the battery unit; the x-axis), a second Rx coil 2230*b* surrounding the magnetic body of the driving unit in the direction of the widthwise minor axis of the microrobot (e.g., the y-axis) perpendicular to the major axis, and a third Rx coil 2230*c*** surrounding the magnetic body of the driving unit in the direction of an axis (e.g., the z-axis) perpendicular to both the lengthwise and widthwise axes of the microrobot. In this case, the magnetic body of the driving unit may have a hexahedral shape.

2-2. Identification of Motion Control and Position Recognition Synchronization FIG. 10 illustrates a flowchart of a technique for synchronizing motion control and position recognition of a microrobot according to an embodiment of the present disclosure.

Figure 10:
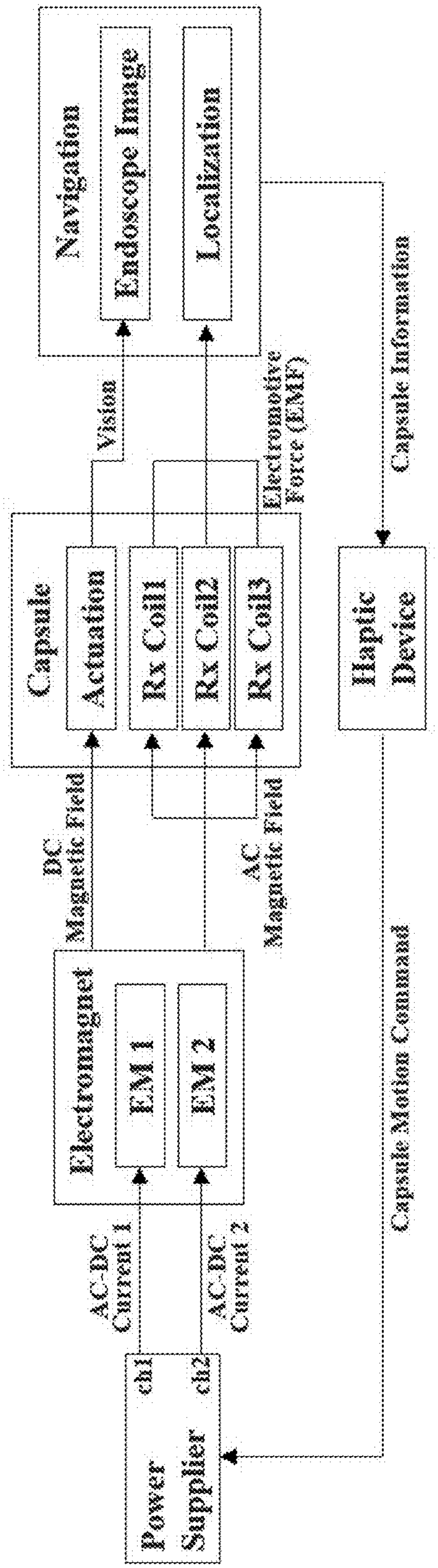
FIG. 10 illustrates a flowchart of a method for synchronizing motion control and position recognition of a microrobot according to an embodiment of the present disclosure.

Referring to FIG. 10, the technique for synchronizing motion control and position recognition of a microrobot is performed by the electromagnetic field system of the present disclosure, and may include: a current application step S100 of independently applying a current from a power supplier to each of a first hybrid electromagnet module and a second hybrid electromagnet module; a steering step S200 of controlling the motion of the microrobot by using a direct current magnetic field generated from the first hybrid electromagnet module and the second hybrid electromagnet module; a reflected signal reception step S300 of receiving, via a communication module, a reflected signal generated by an Rx module included in the microrobot by using an alternating current magnetic field generated from the first hybrid electromagnet module and the second hybrid electromagnet module; and a position recognition step S400 of recognizing a position of the microrobot by using the reflected signal.

The technique for synchronizing motion control and position recognition of a microrobot applies integrated currents, each including a direct current (DC) and an alternating current (AC), to dual hybrid electromagnets EM1 and EM2 through two channels ch1 and ch2 of the power supplier of the electromagnetic field system, respectively, to generate a DC-AC integrated magnetic field in the dual hybrid electromagnets. Under the DC-AC integrated magnetic field condition, a DC magnetic field may react with the permanent magnet 2210 of the microrobot (capsule endoscope) 2000 to induce the motion of the microrobot (S200).

At the same time, an AC magnetic field reacts with the three-axis Rx module (Rx Coil 1, Rx Coil 2, and Rx Coil 3) 2230 of the microrobot to induce electromotive force (EMF). Procedure video image information is generated through the camera unit 2400 embedded in the microrobot, and electromotive force (EMF) information is generated from the 3-axis Rx module. The information is transmitted to a navigation PC (not shown) via the wireless communication module 2300 and converted into a procedure video and position information of the microrobot, which can be visually identified by a user (S300, S400). The conversion process will be described later in FIG. 11. By identifying the procedure video and position information of the microrobot, the user can manipulate a haptic device for subsequent procedure operation, i.e., changing the posture of the microrobot or changing the direction of the camera unit, and manipulation information generated by the haptic device is transmitted to the power supplier. The direct current may be changed in real time on the basis of the manipulation information, but the alternating current is fixedly applied with a predetermined frequency and magnitude for position recognition. This makes it possible to control the driving of the microrobot.

In this regard, the conversion step may additionally include a display step S500 of displaying the position information of the microrobot to the user by using a separately provided display device or the like. Furthermore, the display step may additionally include a manipulation step S600 of receiving driving information of the microrobot generated by a user' manipulation of a separately provided haptic device. The driving information of the microrobot may be transmitted to the power supplier.

Figure 11:
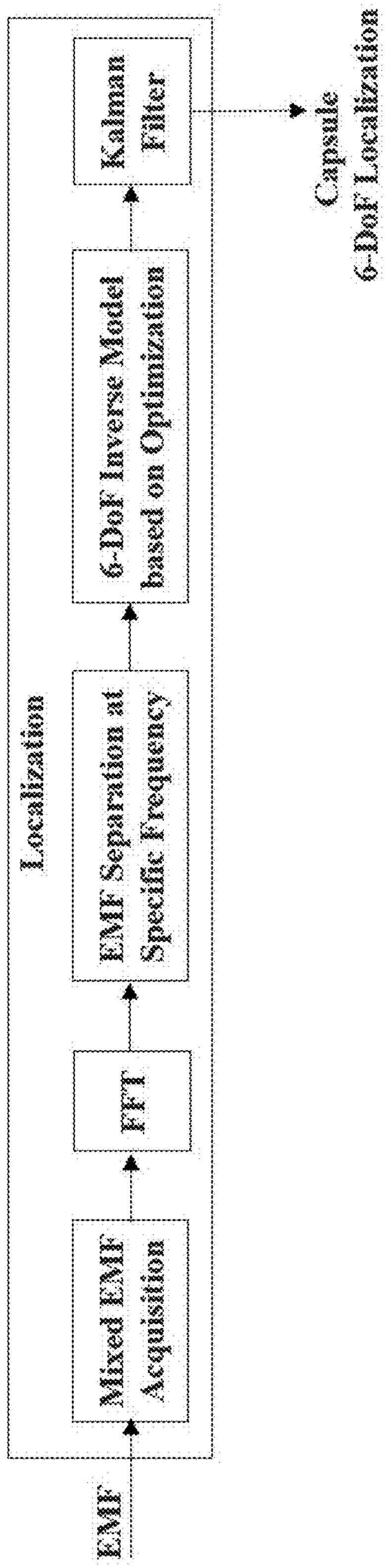
FIG. 11 illustrates a flowchart of a method of recognizing the position of a microrobot by utilizing electromotive force (EMF) induced through a AC magnetic field.

FIG. 11 illustrates a flowchart of a method of recognizing the position of a microrobot by utilizing electromotive force (EMF) induced through a DC magnetic field.

Referring to FIG. 11, induced electromotive force (EMF) is induced in the form of mixed EMF in the three-axis Rx module 2230 via the AC magnetic field of each of the dual hybrid electromagnets EM1 and EM2. The AC magnetic fields of the electromagnets EM1 and EM2 have different specific frequencies and magnitudes, and these features are represented in the form of a mixed signal in the induced electromotive force of the three-axis Rx module (S300). The mixed signals of the electromotive force may be distinguished by frequency through the fast Fourier transform (FFT) technique. The distinguished frequency-specific electromotive force signals may be converted into position information by using the 6 DoF inverse model, and may pass through a Kalman filter to remove noise, and finally, 6 DoF microrobot position information may be obtained (S400).

Figure 12:
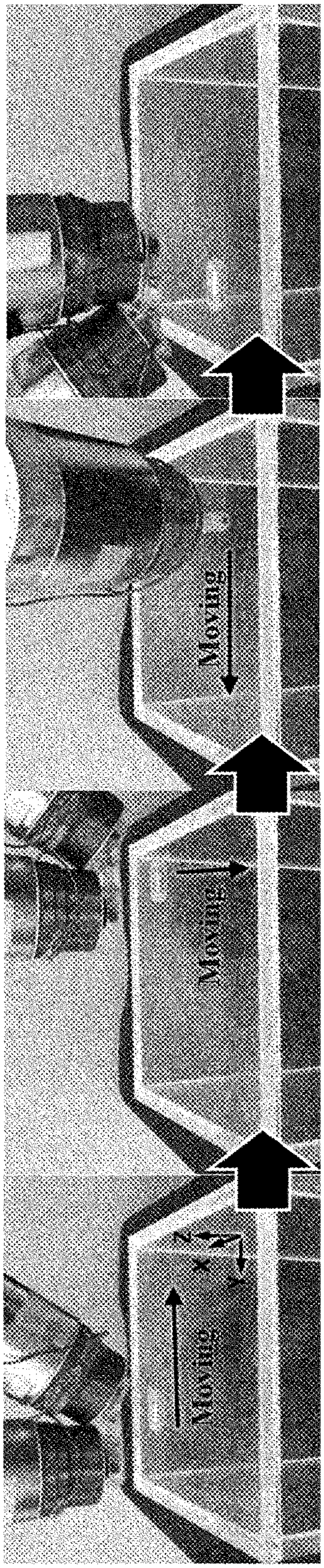
FIG. 12 is a photograph of the motion of a capsule endoscope implemented through the generation of an AC-DC magnetic field by dual hybrid electromagnets according to an embodiment of the present disclosure.

FIG. 12 is a photograph of the motion of a capsule endoscope implemented through the generation of an AC-DC magnetic field by dual hybrid electromagnets according to an embodiment of the present disclosure. It was identified that the dual hybrid electromagnet modules may drive a microrobot by moving in space while simultaneously moving an intersection point where the central axis of the first hybrid electromagnet module intersects the central axis of the second hybrid electromagnet module.

Figure 13:
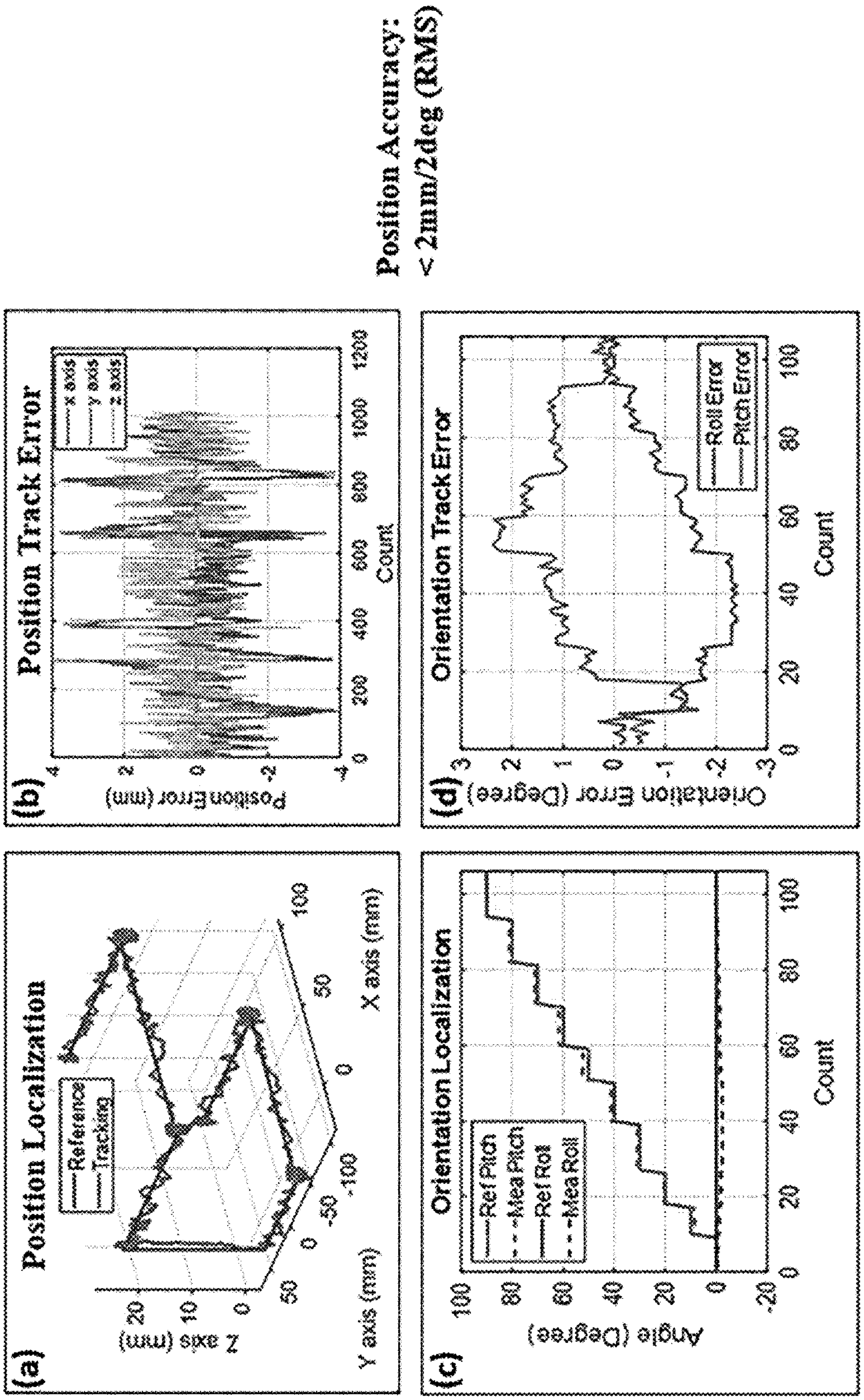
FIG. 13 illustrates the results of capsule endoscope position recognition, obtained in real time while a capsule endoscope operates.

FIG. 13 illustrates the results of capsule endoscope position recognition, obtained in real time while a capsule endoscope operates.

Referring to FIG. 13, it can be found that when compared with the predetermined positional and angular paths (Reference), the real-time acquired capsule endoscope position information (Tracking) is similar to the Reference. As a result, based on RMS, the microrobot was found to have a position error of less than 2 mm and an angular error of less than 2 degrees.

The present disclosure described above is not intended to be limited by the foregoing embodiments and accompanying drawings, as various substitutions, modifications, and changes can be made by a person skilled in the art to which the invention belongs without departing from the technical idea of the present disclosure.

| Description of Symbols |
|---|
| 100: First hybrid electromagnet module |
| 110: First magnetic body |
| 115: First permanent magnet |
| 120: First electromagnet |
| 121: First magnetic core |
| 200: Second hybrid electromagnet module |
| 210: Second magnetic body |
| 215: Second permanent magnet |
| 220: Second electromagnet |
| 221: Second magnetic core |
| 20: Central axis |
| 30: Intersection point |
| 300: Frame |
| 400: Body unit |
| 500: Arm |
| 600: Bed |
| 1000: Electromagnetic field system |
| 2000: Microrobot |
| 2100: Housing |
| 2200: Motion control and position information provision unit |
| 2210: Driving unit |
| 2210a: S pole of driving unit |
| 2210b: N pole of driving unit |
| 2230: Position information provision unit |
| 2230a, 2230b, 2230c: Three-axis Rx module |
| 2300: Data transceiver |
| 2400: Camera module |
| 2500: Battery unit |
| S100: Current application step |
| S200: Steering step |
| S300: Reflected signal reception step |
| S400: Position recognition step. |

INDUSTRIAL APPLICABILITY

Accordingly, the present inventors have found that the method for synchronizing motion control and position recognition of a microrobot according to the present disclosure may synchronize accurate control of a microrobot and position recognition of the microrobot.

Accordingly, an aspect of the present disclosure is to provide a method for synchronizing motion control and position recognition of a microrobot.

What is claimed is:

1. A method for synchronizing motion control and position recognition of a microrobot, performed using an electromagnetic field system in which electromagnet modules are arranged such that central axes of the electromagnet modules intersect to form an intersection point, the method comprising:

a current application step of independently applying a current from a power supplier to each of a first hybrid electromagnet module and a second hybrid electromagnet module;

a steering step of controlling a motion of the microrobot by using a direct current magnetic field generated from the first hybrid electromagnet module and the second hybrid electromagnet module;

a reflected signal reception step of receiving, via a communication module, a reflected signal generated by an Rx module included in the microrobot by using an alternating current magnetic field generated from the first hybrid electromagnet module and the second hybrid electromagnet module; and a position recognition step of recognizing a position of the microrobot by using the reflected signal.

2. The method of claim 1, wherein the electromagnetic field system comprises: a first hybrid electromagnet module; and a second hybrid electromagnet module, the first hybrid electromagnet module comprises a first magnetic body comprising a first permanent magnet, and a first electromagnet comprising a first magnetic core and a first wire wound on the first magnetic core, the second hybrid electromagnet module comprises a second magnetic body comprising a second permanent magnet, and a second electromagnet comprising a second magnetic core and a second wire wound on the second magnetic core, and the first hybrid electromagnet module and the second hybrid electromagnet module are arranged such that a central axis of the first hybrid electromagnet module and a central axis of the second hybrid electromagnet module intersect to form an intersection point.

3. The method of claim 1, wherein the current is a direct current-alternating current integrated current (DC-AC) comprising a direct current (DC) and an alternating current (AC).

4. The method of claim 1, wherein the Rx module is a three-axis Rx module.

5. The method of claim 1, wherein the position recognition step comprises:

an extraction step of separating/extracting a frequency-specific signal from a mixed signal; and a conversion step of converting the frequency-specific signal into microrobot position information by using a 6 DoF inverse model.

6. The method of claim 5, wherein the extraction step is performed using a fast Fourier transform (FFT) algorithm.

7. The method of claim 6, wherein the conversion step further comprises a noise removal step, and in the noise removal step, noise is removed from the microrobot position information by using a Kalman filter.

* * * * *